(12) United States Patent
Loupas

(10) Patent No.: US 7,815,572 B2
(45) Date of Patent: Oct. 19, 2010

(54) FLOW SPECTROGRAMS SYNTHESIZED FROM ULTRASONIC FLOW COLOR DOPPLER INFORMATION

(75) Inventor: Thanasis Loupas, Athens (GR)

(73) Assignee: Koninklijke Philips Electronics N.V., Eindhoven (NL)

( * ) Notice: Subject to any disclaimer, the term of this patent is extended or adjusted under 35 U.S.C. 154(b) by 765 days.

(21) Appl. No.: 10/543,031

(22) PCT Filed: Feb. 3, 2004

(86) PCT No.: PCT/IB2004/000264

§ 371 (c)(1),
(2), (4) Date: Jul. 21, 2005

(87) PCT Pub. No.: WO2004/072676

PCT Pub. Date: Aug. 26, 2004

(65) Prior Publication Data

US 2006/0052698 A1 Mar. 9, 2006

Related U.S. Application Data

(60) Provisional application No. 60/447,531, filed on Feb. 13, 2003.

(51) Int. Cl.
*A61B 8/00* (2006.01)

(52) U.S. Cl. .................... 600/441; 600/455

(58) Field of Classification Search .............. 600/443, 600/441, 455; 382/128
See application file for complete search history.

(56) References Cited

U.S. PATENT DOCUMENTS

| | | | |
|---|---|---|---|
| 5,471,990 A | | 12/1995 | Thirsk |
| 5,515,857 A | * | 5/1996 | Tsujino et al. .............. 600/456 |
| 5,622,174 A | * | 4/1997 | Yamazaki .................. 600/441 |
| 5,634,465 A | | 6/1997 | Schmiesing et al. |
| 5,941,826 A | * | 8/1999 | Goujon ...................... 600/451 |
| 6,142,943 A | * | 11/2000 | Mo et al. .................... 600/447 |
| 6,464,637 B1 | | 10/2002 | Criton et al. |
| 6,464,640 B1 | * | 10/2002 | Guracar et al. .............. 600/453 |
| 6,491,636 B2 | | 12/2002 | Chenal et al. |
| 2002/0116141 A1 | * | 8/2002 | Mo et al. ...................... 702/76 |

\* cited by examiner

*Primary Examiner*—Brian Casler
*Assistant Examiner*—Jonathan G Cwern
(74) *Attorney, Agent, or Firm*—W. Brinton Yorks, Jr.

(57) ABSTRACT

An ultrasonic diagnostic imaging system and method are described by which a user can delineate a region of interest (122, 128) in a colorflow Doppler image. The ultrasound system processes the Doppler pixel information of the region of interest (122, 128) to produce a spectrogram illustrating motion at the region of interest (122, 128) as a function of time. In a preferred embodiment the Doppler pixel information is processed by histograms to produce the spectrogram data.

18 Claims, 4 Drawing Sheets

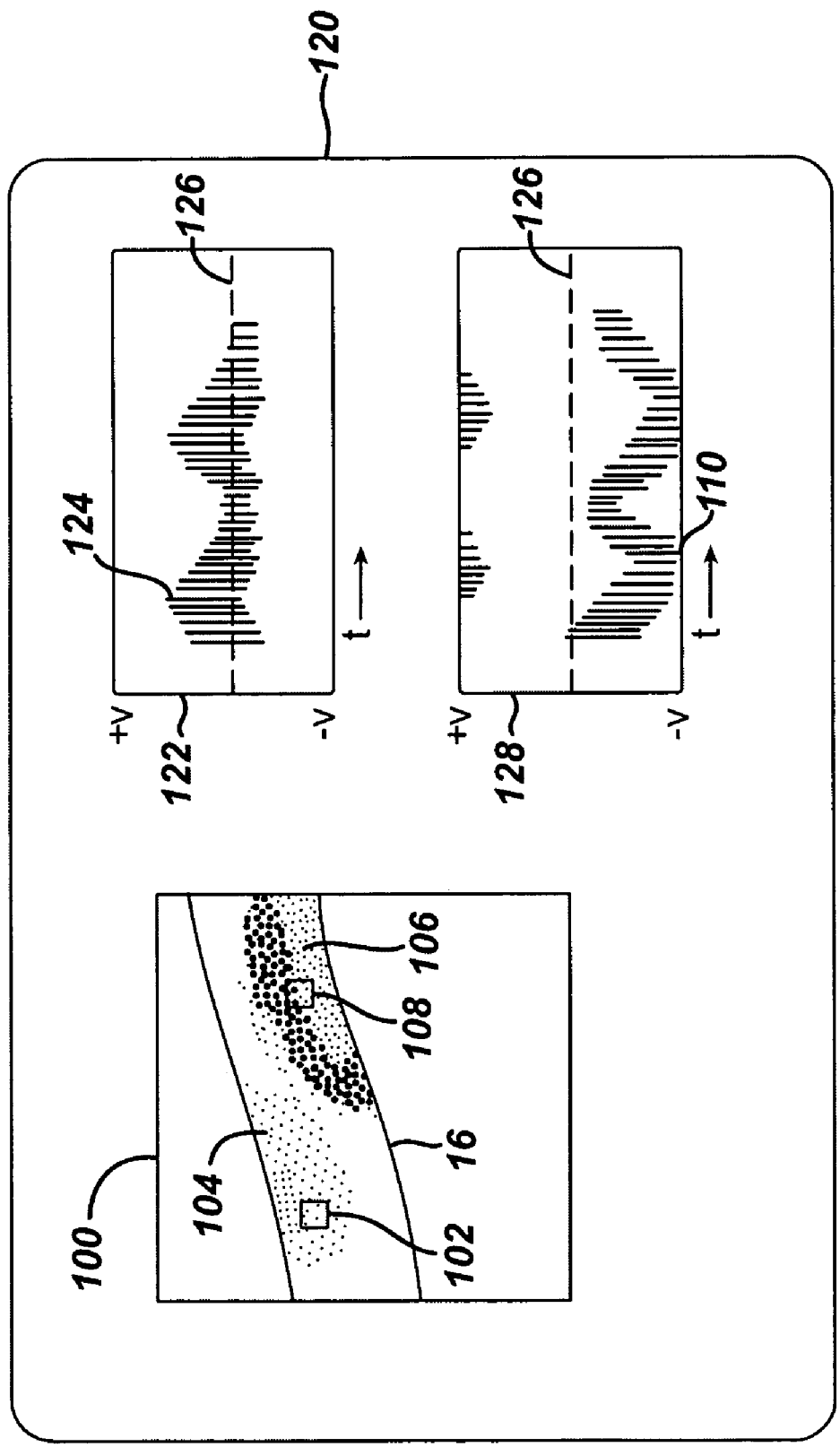

FLOW SPECTROGRAMS SYNTHESIZED FROM ULTRASONIC FLOW COLOR DOPPLER INFORMATION

CROSS REFERENCE TO RELATED APPLICATION

This application claims the benefit of U.S. provisional application Ser. No. 60/447,531 filed Feb. 13, 2003, which is incorporated herein by reference.

This invention relates to ultrasonic diagnostic imaging and, more particularly, to ultrasonic diagnostic imaging systems in which colorflow Doppler information is used to produce synthesized flow spectrograms.

Colorflow Doppler is an ultrasonic imaging mode which has been in widespread use for the past twenty years. Prior to the advent of colorflow Doppler, blood flow was analyzed audibly or through spectral Doppler, which produced a graph of flow velocity or frequency as a function of time at a particular point in the body. Colorflow gave the clinician a much better appreciation of the flow dynamics in the body, as the velocity of blood flow is shown in a spatial representation against the vasculature in which it is contained, with different colors or intensities illustrating the speed and direction of blood flow. More recently, ultrasonic Doppler techniques have been extended to detection, display and measurement of tissue motion, primarily. to study the moving heart and vascular walls. Analysis of tissue motion is performed by means of spectral Doppler as wells as color Doppler imaging techniques.

Since the Doppler shift is being estimated at a large number of points in the image field, the time required to acquire the ultrasound data for one colorflow image is relatively long. This is because the Doppler technique requires each point where flow is to be determined to be sampled numerous times (ensemble length) at a chosen sampling rate (pulse repetition frequency, or PRF.) Consequently the frame rate of display during the colorflow mode is generally relatively low. Various techniques have been offered to allow the clinician to increase the frame rate, such as allowing the image sector in which colorflow is to be acquired to be narrowed, or a "color box" to be defined as the area of the image where colorflow is to be acquired. A third technique is to reduce the number of signal samples (ensemble length) used at each point where the Doppler shift is to be estimated. This, however, causes the flow estimates to become coarser and less highly resolved.

As a consequence of these factors, colorflow is generally used as a survey tool to give the clinician a qualitative appreciation of the flow conditions in the region being imaged. Once the clinician spots a point in the image where the color does not appear as it should or momentarily differs from its usual appearance, the clinician will then turn to spectral Doppler for quantitative analysis. Spectral Doppler, with its much higher sampling rate directed at a single point in the body, then produces a highly resolved spectrum of the changing Doppler shifts (frequency or flow velocity) at that point. This is because the spectral Doppler signals are received virtually continuously from the point at which the measurement is being made. A point in a color box of a colorflow display of, for example, 32 scanlines in width, is only sampled 1/32 of the scanning time, since all of the scanlines in the color box have to be repetitively sampled in order to form the Doppler display in the color box. This also creates a temporal discontinuity between successive frames of colorflow images. With only a limited amount of time available for each scanline, the ensemble lengths for Doppler shift estimation are relatively short in colorflow, often less than ten samples, whereas the ensemble window of a spectral Doppler processor can approach one hundred samples. As a result, a spectral Doppler display can be expected to have better signal-to-noise and better spectral resolution than a point in a typical real-time colorflow display.

The spectral Doppler measurement may be made by holding the ultrasound probe steady against the body of the patient, freezing the colorflow image on the screen, manipulating a sample volume cursor to the position in the colorflow image where the spectral measurement is to be taken, then acquiring the spectral Doppler information in real time. If the probe is moved relative to the desired sample volume, however, a live colorflow image must be reacquired so that the sample volume can be repositioned at the desired anatomy. To obviate this need, the colorflow display and the spectral Doppler acquisition can be performed in a duplex mode, whereby the colorflow display is periodically updated while the spectral Doppler image is being displayed. The colorflow signal acquisition will interrupt the stream of spectral Doppler data in this mode, causing degradation of the signal-to-noise and spectral resolution of the spectral display.

To alleviate these difficulties, researchers have devised a more spatially directed form of colorflow called color M-mode. In color M-mode Doppler information is acquired continuously along a single scanline as in spectral Doppler, thus affording the advantage of a high sampling rate. The data is then color-encoded and displayed in a time sequence of lines as is done in M-mode. While addressing the temporal discontinuity problem mentioned above, color M-mode introduces its own limitations such as the difficulty of appreciating color-encoding as a waveform, and the one-dimensional spatial nature of the display. Accordingly, it is desirable to develop other ways to use colorflow information to better afford the type of dynamic, quantifiable information provided by spectral Doppler displays.

In accordance with the principles of the present invention, color Doppler imaging data is used to document the distribution of characteristic motion features (such as velocity, acceleration, temporal and/or spatial velocity derivatives) as a function of time in a two-dimensional image with one axis representing time and the other axis corresponding to the specific motion feature being mapped. The color Doppler imaging data of a selected group of pixels is processed to produce a one-dimensional distribution of display parameters characterizing blood flow or tissue motion at the pixel locations at the time of the colorflow frame. The resultant display can be a spectrogram similar to a spectral Doppler display. In a preferred embodiment a histogram is formed from the colorflow data and mapped to the desired display parameter. A temporal sequence of display parameters over the interval of a sequence of colorflow frames illustrates the flow dynamics at the pixel locations over part or all of a heart cycle.

In the drawings:

FIG. 6 illustrates an ultrasound display constructed in accordance with the principles of the present invention.

Figure 1:
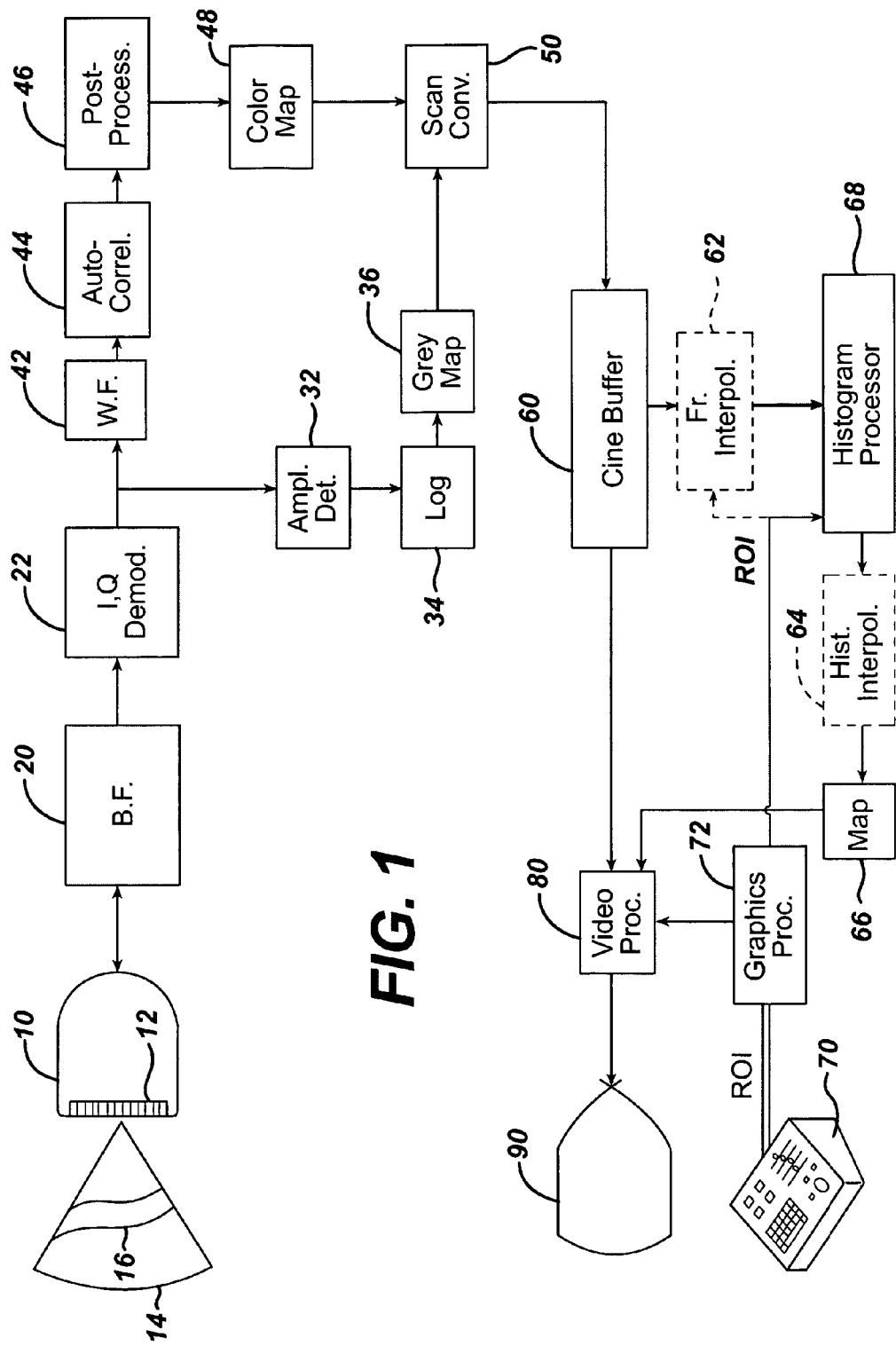
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. An ultrasonic probe 10 has an array transducer 12 which transmits ultrasonic waves over an image field 14 in the body. In this illustration the image field 14 is shown as sector-shaped as would be scanned by a phased array transducer. The illustrated sector image includes a blood vessel 16 which is being interrogated by the probe. If a two dimensional image plane is to be scanned the array will comprise a one-dimensional array of transducer elements, and if elevation focusing is used or a three dimensional volume is to be scanned in real time, the array will comprise a two-dimensional array of elements. Echoes from the transmitted waves are received by the array transducer, converted into electrical signals, and coupled to a beamformer 20. In the beamformer the signals from the elements of the array transducer are delayed and combined to form steered and focused beams of sequences of echo signals from depth locations along the beam directions. The echo signals are coupled to an I,Q demodulator 22 which detects quadrature components of the echo signals.

The quadrature signal components can be processed in two signal paths: a B mode signal path and a Doppler signal path. In the B mode signal path the I,Q signals undergo detection by an amplitude detector 32. The detected signal are logarithmically compressed by a log compressor 34 and are then mapped by a look-up table to the corresponding values of a desired greyscale map 36. The greyscale image signals are then coupled to a scan converter 50, which smoothes the image information and converts the image signals to the desired image format. In the Doppler signal path the I,Q signals are filtered by a wall filter 42 to remove any unwanted signals such as tissue signals when flow is being imaged. The Doppler shift is then estimated. A preferred Doppler estimator is an auto-correlator 44, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. The velocity and power estimates undergo threshold detection to reduce noise, segmentation and post-processing such as hole filling and smoothing in a post-processor 46. The velocity and power estimates are mapped to a desired range of display colors by a color map 48. The color values are applied to the scan converter 50 where they are converted to the desired image format and overlaid on the B mode image of the tissue structure containing the blood flow to form a colorflow image.

The colorflow images are applied to a Cineloop® buffer 60, which stores the most recent sequence of acquired images. The number of images stored in the Cineloop buffer depends upon the size of the storage device used. A display frame is coupled from an output of the Cineloop buffer to a video processor 80. The point at which the display frame is tapped off from the Cineloop buffer may be at the beginning, the end, or at an intermediate point of the frame sequence stored in the buffer. The video processor responds to a display frame by producing the necessary display drive signals to display the colorflow image on a display 90.

In accordance with the principles of the present invention, the embodiment of FIG. 1 includes circuitry for producing a spectrogram from the colorflow image data. An output of the Cineloop buffer 60 is coupled to the input of an optional frame interpolator 62. The frame interpolator 62 is used when it is desired to interpolate additional frame data between the processed colorflow frames, thereby increasing the temporal resolution of a spectrogram. The frame interpolator can interpolate additional complete image frames, or only the colorflow data of a region of interest (ROI) as discussed below. The output of the frame interpolator 62 is coupled to a histogram processor 68. The histogram processor forms a histogram of the colorflow data of a selected ROI as discussed below. The output of the histogram processor 68 is coupled to an optional histogram interpolator, which can interpolate additional histogram data sets between those produced by the histogram processor so as to increase the temporal as well as frequency/velocity resolution of the spectrogram. The histogram interpolator 64 can be used instead of the frame interpolator 62; in a constructed embodiment both a frame interpolator and a histogram interpolator are used to increase temporal resolution. The output of the histogram interpolator 64 is coupled to a map, where the histogram data is mapped to the desired form of color or greyscale display lines. The display lines are coupled to the video processor 80 for display as discussed below.

The ultrasound system of FIG. I also has a control panel 70, from which the various functions of the system are controlled and operated by a user. Associated with the present invention is a control for selecting an ROI on a colorflow image. An image designation of the ROI such as the outline of the ROI is produced by a graphics processor 72 and coupled to the video processor 80 for overlay with the colorflow image. The coordinates of the ROI are coupled to the histogram processor 68 for selection of the data to be used in a histogram, and optionally also to the frame interpolator 62 for use when only the frame data of the ROI is to be interpolated by the interpolator 62.

In operation, the user manipulates a control on the control panel 70 such as a joystick or trackball to define a region of interest on an ultrasound grayscale or flow image. The defined ROI specifies the spatial locations from which Doppler or, more generally, motion signals will be acquired. The defined ROI can have a predetermined shape such as a rectangle or ellipse, or a square or circle for a two dimensional image or a box or ball for a three dimensional image. The ROI can be have arbitrary, user-defined shape such as a free form polygon or spline shape. Multiple ROIs can be defined as illustrated below. The purpose of the ROI is to encompass or define a plurality of pixel locations from which data is to be processed in accordance with the present invention. The ROI can be defined over a live, real time image, or can be defined over a stored image such as one that has been saved in the Cineloop buffer.

Figure 2:
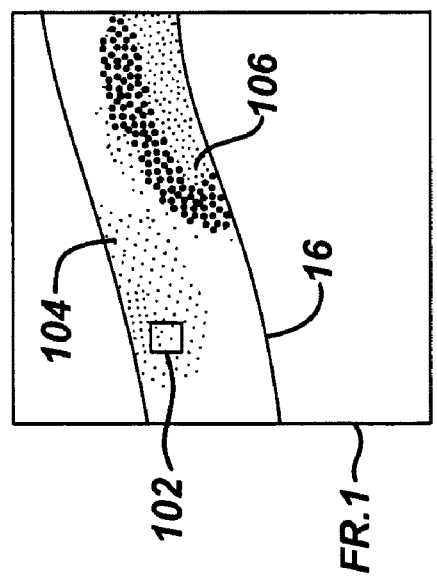
FIG. 2 illustrates a colorflow image frame showing a blood vessel and a selected spectrogram sample volume.

For the case where the system of FIG. I operates on stored image data, operation proceeds as follows. While observing real time colorflow images, the user presses the control panel "Freeze" button to freeze the current image on the display screen and retain a sequence of colorflow images in the Cineloop buffer 60. Alternately, the user can read a sequence of previously-stored images into the buffer 60 with one of the images displayed on the display screen. The user manipulates the user control so that the ROI is of the desired shape and size and is positioned over the flow which is to be measured. For example, the ROI may initially appear as a small square 102 in the image frame, as shown in FIG. 2. The user may drag the ROI square until it is over a flow area to be diagnosed. The user may stretch or compress the square to a different size or shape that outlines the flow to be diagnosed. In the example of FIG. 2, the user has positioned the ROI 102 over a flow area 104 in blood vessel 16 of particular interest. The shaded areas 104 and 106 in the blood vessel 16 represent colored areas of the colorflow image frame where flow activity of interest is occurring.

Figure 3:
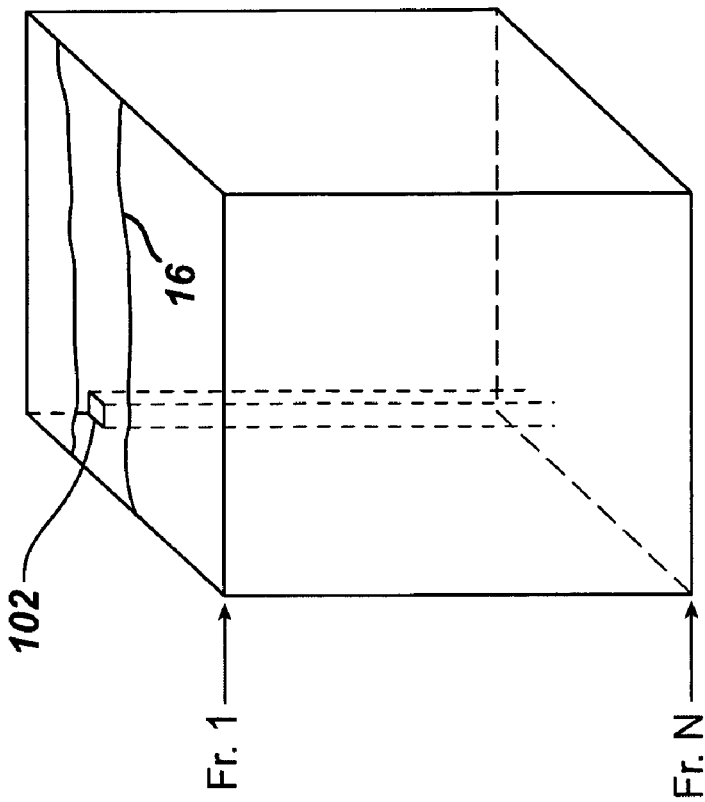
FIG. 3 illustrates a sequence of colorflow image frames arranged in a stack.

The ROI 102 delineates a plurality of colorflow pixels in an image Frame I which will be analyzed in accordance with the present invention. The same spatial ROI delineates corresponding flow pixels in the other images of the image sequence stored in the Cineloop buffer 60, as represented by the stack of image frames shown in FIG. 3. The frame on top of the stack is Frame 1 and the frame on the bottom of the stack is Frame N. As the drawing illustrates, the ROI 102 is effectively projected through all of the image frames in the stack, thereby delineating a plurality of pixels in each image which will be analyzed for its particular image frame.

The image frames in the Cineloop buffer 60 are submitted to the histogram processor 68 for processing. However, the temporal spacing of the image frames in the sequence may be too great for the temporal resolution desired for the spectrogram. To improve the temporal resolution of the data for the spectrogram, additional frames are interpolated between those that are present in the buffer 60. The interpolation may be a simple linear interpolation between two frames. For instance a pixel at location $x_m, y_n$ in Frame 3 may have a velocity value of 6 when that frame occurs at time t=3, and the pixel at location $x_m, y_n$ in Frame 4 may have a velocity value of 8 when that frame occurs at time t=4. The frame interpolator 62 could linearly interpolate a temporally intermediate Frame 3.5 for time t=3.5 in which the pixel at location $x_m, y_n$ in interpolated Frame 3.5 has a velocity value of 7. Nonlinear interpolation functions (such as circular interpolation suitable for aliased velocity values) may also be used, and multiple frames can be interpolated between the frames of the Cineloop buffer. To reduce the interpolation processing required, the frame interpolator 62 may only interpolate additional frame values for the pixels of the ROIs of the frames, as those are the values used by the histogram processor 68.

The received frames and any interpolated frames are submitted to the histogram processor 68. The data of each ROI pixel that is analyzed is the velocity data, the power Doppler data, or some other selected value relating to motion. In the present example, both the velocity and the power data are used in the analysis. The power and velocity (or velocity-related) estimates corresponding to a desired temporal analysis interval T are stored in data arrays V(k) and P(k), where k=1, 2, ... K, and K is determined by the number of ROI pixels supplied to the histogram processor. If the spectrogram is created in conjunction with a standard motion imaging mode (Color Doppler, Color Power Angio, Tissue Doppler Imaging, etc.), an obvious choice for the temporal analysis interval T would be the frame acquisition interval, including the effective acquisition interval of an interpolated frame. Alternatively, the scanning sequence can be modified to include more frequent acquisitions for beams passing through the ROI, thus offering temporal analysis intervals that are a fraction of the frame acquisition interval. An example of this would be to time-interleave repetitive scanning of beams passing through the ROI while the scanlines of the image frame outside the ROI are being acquired. When the spectrogram is created in conjunction with a standard motion imaging mode, the standard estimates used in the motion imaging modes can be used without modification, thus producing one temporal sample per ensemble corresponding to the mean velocity/power within the ensemble. Each frame thus has a single temporal sample resulting from motion processing of the ensemble of samples. Alternatively, the spectrogram data can be obtained from dedicated power and velocity (or velocity-related) estimates operating on subsets of the original ensemble sequences, thus producing more than one temporal samples per input ensemble and offering more instantaneous (instead of more averaged) estimates.

The V(k) and P(k) data arrays are used to produce a one-dimensional array A( ) characterizing motion within the temporal interval T. There are numerous ways in which the data arrays may be used or combined. For example, the array A( ) can be the velocity distribution $A(v_m)$, equal to the number of occurrences of the velocity range $v_m$ in array V(k). One way of calculating this is:

For all $v_m$ values of interest, set $A(v_m)=0$.

For each k, find the velocity range $v_m$ corresponding to V(k) and,

If $v_m$ is among the values of interest, set $A(v_m)=A(v_m)+1$.

A numeric example of this technique is to assume an ROI of two pixels by two pixels (=four pixels). The V(k) and P(k) arrays thus have four elements each, which are assumed to be V={−41,−45,−22,+47} and P={10,8,5,9}. The V array units are cm/sec and the P array units are log-compressed power units. Further assume that the histogram velocity ranges extend from −50 cm/sec to +50 cm/sec in steps of 20 cm/sec. This would result in a velocity distribution of:

| | |
|---|---|
| A(1) corresponds to velocity range | v1 = [−50, −30]; |
| A(2) corresponds to velocity range | v2 = [−30, −10]; |
| A(3) corresponds to velocity range | v3 = [−10, +10]; |
| A(4) corresponds to velocity range | v4 = [+10, +30]; |
| A(5) corresponds to velocity range | v5 = [+30, +50); |

The correspondence of the velocity values of V and the histogram velocity ranges is:

| | |
|---|---|
| −41 cm/s is in range | v1; |
| −45 cm/s is in range | v1; |
| −22 cm/s is in range | v2; |
| +47 cm/s is in range | v5; |

Therefore the elements of A are:

A(1)=1+1=2;

A(2)=1;

A(3)=0;

A(4)=0;

A(5)=1

As another example, the array A( ) can be the power-weighted velocity distribution $A(v_m)$, equal to the sum of powers P(k) corresponding to all occurrences of the velocity range $v_m$ in array V(k). One way of calculating this is:

For all $v_m$ values of interest, set $A(v_m)=0$.

For each k, find the velocity range $v_m$ corresponding to V(k) and, if $v_m$ is among the values of interest, set $A(v_m)=A(v_m)+G[P(k)]$ where G[ ] is a function designed to provide the desired power weighting (linear, piece-wise linear, square root, logarithmic compression, etc.). A numeric example of this technique, using the above numeric examples for the V and P arrays, shows that:

| | |
|---|---|
| −41 cm/s is in range | v1 and is associated with power 10; |
| −45 cm/s is in range | v1 and is associated with power 8; |
| −22 cm/s is in range | v2 and is associated with power 5; |
| +47 cm/s is in range | v5 and is associated with power 9; | and therefore the elements of A are:
A(1)=G[10]+G[8]=18;
A(2)=G[5]=5;
A(3)=0;
A(4)=0;
A(5)=G[9]=9

More generally, the array A( ) can represent any alternative means of documenting statistical distributions (such as dot-plots, stemplots, boxplots, etc.). Furthermore, the array A( ) can be any function that depends on mathematical combinations of statistical distribution properties in order to convey information similar to the histogram. Examples of statistical distribution properties related to the histogram and suitable for display are measures of central location (such as mean, mode or median), measures of dispersion (such as standard deviation, mean absolute difference, min/max values, percentile range, etc.) or measures of shape (skewness, kurtosis, etc).

Figure 4:
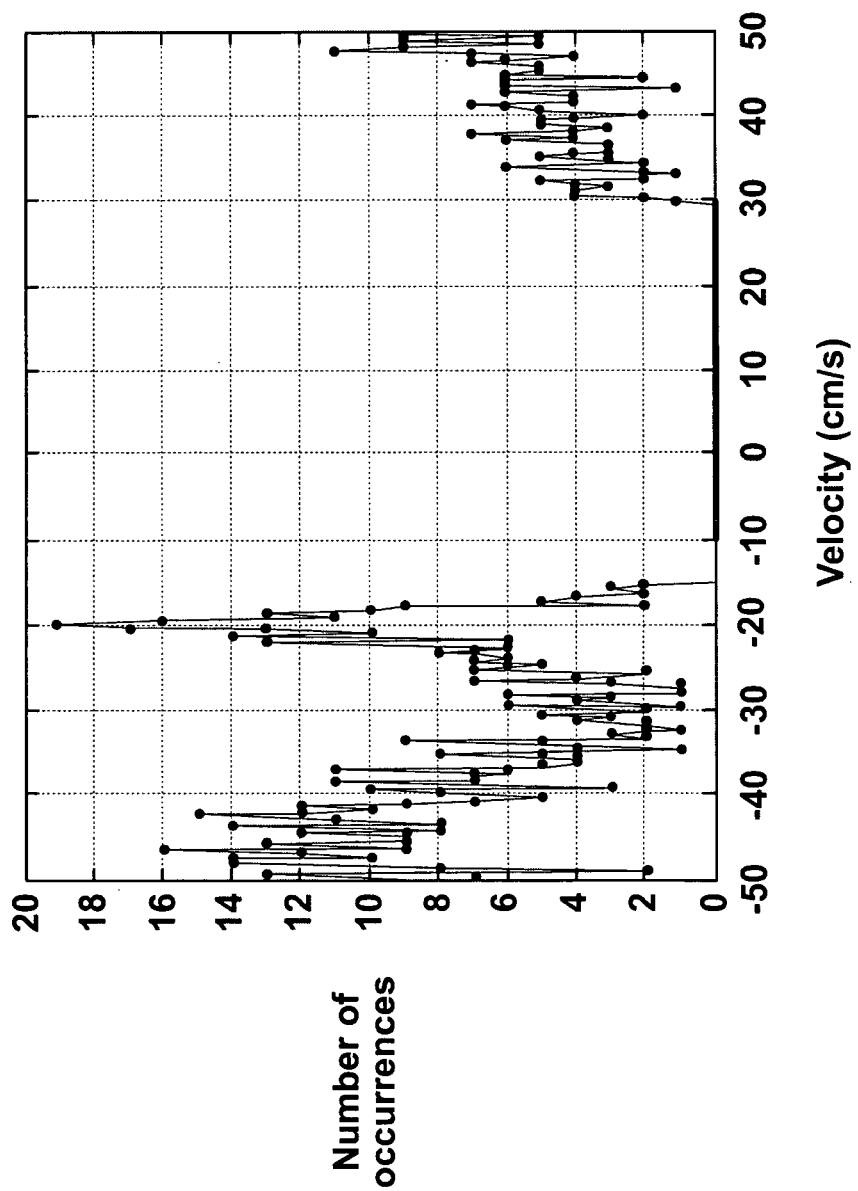
FIG. 4 illustrates a histogram for a 30 pixel by 30 pixel sample volume.

FIG. 4 illustrates an example of a velocity histogram using the first technique described above. The data is from an ROI of thirty pixels by thirty pixels in a given image frame, and thus the V(k) array has a size of 900 samples. The Nyquist velocity range of the histogram scale is 100 cm/sec, with a maximum positive velocity of 50 cm/sec and a maximum negative velocity of −50 cm/sec. The ordinate axis indicates the number of pixels exhibiting a velocity of one of the velocities represented on the abscissa axis. For instance, nineteen of the nine hundred pixels have a velocity value of −20 cm/sec. The distribution of velocities in the ROI is seen to be predominately negative velocities from −15 cm/sec to −50 cm/sec. The absence of any velocity values in the center of the scale and the occurrences at the right of the histogram which decline from +50 cm/sec to +30 cm/sec indicate that aliasing has occurred for the Nyquist range utilized, and that negative velocities greater than −50 cm/sec have wrapped around to appear at the right side of the histogram.

As histograms such as that shown in FIG. 4 are produced by the histogram processor 68, the temporal resolution of the spectrogram can be increased by interpolating intermediate histograms between those produced by the histogram processor. For instance, if the histogram interpolator 64 receives the histogram of FIG. 4 for Frame 3 at time t=3 and a successive histogram for Frame 4 at time t=4 which shows 13 occurrences of a velocity of −20 cm/sec, an intermediate histogram could be interpolated for time t=3.5 by linear interpolation, which would show 16 occurrences of a −20 cm/sec velocity.

Figure 5:
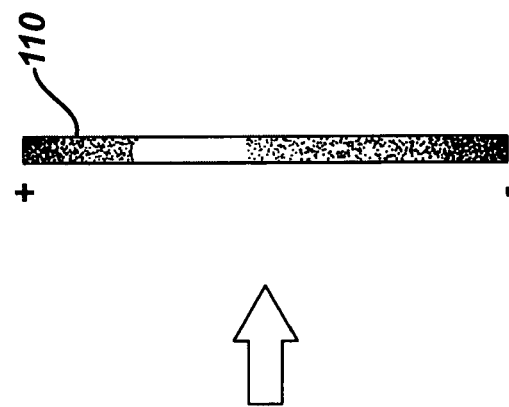
FIG. 5 illustrates a spectrogram display bar mapped from the histogram of FIG. 4.

The data of each histogram is then mapped to a columnar display element for the spectrogram display. One such display element 110 is shown in FIG. 5. As the arrow between FIGS. 4 and 5 indicates, the display element 110 is the sort of display element that would be produced from the histogram data of FIG. 4. The "+" and "−" symbols next to the element 110 show that the histogram data values are mapped with the positive velocity values (e.g., flow toward the transducer) at the top and the negative velocity values (e.g., flow away from the transducer) at the bottom. The darker the display element 110, the greater are the number of occurrences of the particular velocity at that level of the element. While the illustrated mapping is of a greyscale where darker shades indicate a greater number of values, it will be appreciated that, for an ultrasound display which is generally shown by white-on-black, the greater numbers of occurrences would be shown by lighter shades of grey or white. The display element may alternatively be mapped to colors instead of or in addition to intensities. A two-dimensional array B( ) is gradually built up on a column-wise manner. Each column of array B( ) corresponds to a temporal interval T equal to an array A( ) obtained from the analysis of the same temporal interval. Prior to display, the B( ) array is mapped to a grayscale or color image by means of the greylevel or RGB map 66. The scaling involved in the mapping can be automatically or manually adjusted to ensure good utilization of the available greylevels or colors, and minimize mapping artifacts such as saturation. A multiplier may be used if desired to translate the display values to a desired range of values. The mapped display elements 110 of two-dimensional array B( ) are displayed as a spectrogram. If desired, the spectrogram may be accompanied by displayed numeric values such as the maximum or the mean blood flow velocity for each heart cycle.

A typical display 120 for illustrating a spectrogram formed in accordance with the principles of the present invention is shown in FIG. 6. The colorflow image frame 100 on which the ROI or ROIs were placed is shown at the left side of the display, and spectrograms 122 and 128 for the ROIs 102 and 108 are shown at the right side of the display. Each time the user adds another ROI to the image 100 a new spectrogram appears on the display. As the user moves an ROI around on the image or alters its size or shape, the spectrogram for the ROI changes in accordance with the new pixel values delineated by the change to the ROI. Each spectrogram 122,128 appears in this embodiment as a series of columnar lines 124 of velocities displayed over time, in the same manner as the familiar spectral Doppler display. Each columnar line 124 is formed from the pixels in the ROI of one of the successive images used, or images or histograms interpolated therefrom. In a preferred embodiment the columnar lines are shown in relation to a zero velocity baseline 126. The spectrogram 128 is seen to contain columnar line 110 of FIG. 5 in the first aliased region of the display.

The embodiment of FIG. 6 readily lends itself to report generation, as the colorflow image with the illustrated ROI(s) and associated spectrogram(s) can be electronically pasted directly into a clinical report.

When the display 120 is formed from a sequence of stored images, the spectrograms will be static displays, as the colorflow frames stored in the Cineloop buffer which are used to form them are unchanging. The display 120 can also be formed from real time images, in which case the displayed frame 100 will be a live colorflow image that changes in real time. Each time a new colorflow image is produced by the scan converter 50 and shown as image 100, its ROI data is used to produce a histogram which is mapped for a new columnar element on the displayed spectrogram(s). The spectrogram thus produced will therefore most effectively be shown as a real time scrolling display. When real time images are used the signal path for the histogram processor can be simplified by taking the ROI pixel data directly from the color map 48.

The velocity (or velocity-related) range of the B( ) array (and hence the spectrogram) can be automatically or manually adjusted to fit the range of values present in the B( ) array. For example, the default velocity range can be set to (−0.5*NyquistVel, +0.5*NyquistVel), where NyquistVel is the maximum positive or negative velocity that can be measured without aliasing, but could be automatically or manually modified to [−0.1*NyquistVel, +0.9*NyquistVel] for a condition in which the velocities present are predominantly positive. If aliasing is found to occur in a spectrogram such as is the case of display element 110 and its neighboring elements in spectrogram 128, the aliasing condition could be automatically sensed by detecting the absence of values in the center of the display element and the existence of values at the "+" and "−" Nyquist limits of the histogram or display element. The scale of the spectrogram display could be increased, and the "wrapped" values unwrapped for the display. Alternatively, if system control permits, the sensing of the aliasing condition could be fed back to the probe transmit controller and the PRF of the probe increased to eliminate the aliasing.

The principles of the present invention can also be applied to automatically scale a spectrogram (corresponding to the standard spectral Doppler mode, or synthesized from color Doppler data as described in this invention) or other velocity-based display on the ultrasound system (including optimizing the velocity scale of the standard color Doppler mode). A sequence of colorflow images can be captured in the Cineloop buffer and processed as described above. Instead of using one or a few ROIs, the entire flow area of the image can be automatically covered with ROI of, for example, the default ROI size. Histograms are then calculated for all of the ROIs and the histograms processed to detect the maximum and minimum velocity values and the wraparound characteristic of aliasing. If the maximum and minimum velocities of all of the ROIs are very low, the scaling of the spectrogram or velocity-based displays can be reduced to a smaller range. If the maximum and minimum values are at the Nyquist limits and wraparound is detected, the display range can be increased, the baseline can be offset, or the PRF increased accordingly. The resultant display scaling should be adequate for any ROI placed in any area or region of the images.

What is claimed is:

1. A method for producing a spectrogram from a plurality of two or three dimensional ultrasound images depicting motion comprising:
    acquiring a plurality of colorflow ultrasound images comprising motion data where motion is present in the imaged region;
    delineating a region of interest (ROI) in one of the images, the ROI comprising a plurality of spatially discrete pixels of motion data;
    forming histograms of the motion data of the spatially discrete pixels of the ROI in a plurality of images containing the pixel information over a plurality of defined temporal intervals;
    mapping the histograms of the plurality of images to a plurality of temporally discrete lines; and
    displaying the lines as a spectrogram for the ROI.

2. The method of claim 1, wherein the defined temporal intervals comprise frame rate intervals.

3. The method of claim 2, further comprising capturing a sequence of colorflow images in an image buffer.

4. The method of claim 1, wherein the motion data of the pixels of the ROI comprises at least one of velocity information and Doppler power information.

5. The method of claim 1, wherein displaying further comprises displaying a two or three dimensional image on which an ROI is delineated, wherein the spectrogram is concurrently displayed.

6. A method for displaying the distribution of a motion characteristic occurring at a region of interest in a two or three dimensional ultrasound image of the body comprising:
    acquiring a sequence of spatially dimensioned colorflow ultrasound images in which a motion characteristic is displayed by motion data;
    delineating a region of interest (ROI) in one of the images where motion data is present in a plurality of spatially different points in the image;
    processing the motion data from the image points of the delineated ROI of a plurality of images to determine the distribution of a motion characteristic as a function of the time of each. image; and
    displaying the distribution of the motion characteristics of the plurality of images as a plurality of columnar display lines of a spectral display as a function of time.

7. The method of claim 6, wherein the motion characteristic comprises blood flow velocity.

8. The method of claim 7, wherein delineating further comprises delineating a plurality of spatially different pixels in one of the images.

9. The method of claim 8, wherein processing further comprises processing the motion data of pixels spatially corresponding to the ROI in each of the color Doppler images.

10. The method of claim 9, wherein processing further comprises producing a histogram of the motion data of the ROI of each color Doppler image.

11. The method of claim 10, wherein displaying further comprises mapping histogram data to a plurality of temporal display lines, wherein a spectral display of the temporal display lines illustrates the distribution of the motion characteristic as a function of time.

12. The method of claim 6, wherein the motion characteristic comprises blood flow velocity derivatives in the temporal or spatial domain.

13. The method of claim 6, wherein the motion characteristic comprises tissue motion velocity or its derivatives in the temporal or spatial domain.

14. An ultrasonic diagnostic imaging system which provides motion information concerning a location in the body comprising:
    an ultrasound probe which transmits ultrasonic energy and receives ultrasonic echo signals in response;
    a beamformer coupled to the probe which forms coherent echo signals from spatial locations in the body;
    a motion processor responsive to the spatial echo signals which produces image data depicting motion;
    a display responsive to the image data which displays two or three dimensional colorflow images depicting motion on a spatial basis;
    a user control by which a user can delineate a region of interest in a two or three dimensional colorflow image comprising spatially discrete image points depicting motion;
    a motion characteristic processor, responsive to motion information of the image points depicting motion of the region of interest, and configured to process motion data from a plurality of spatially different pixels in the image to produce a temporally discrete histogram of velocity values,
    wherein the display displays the distribution of a motion characteristic of the histogram as a line of a spectral display as a function of time for a delineated region of interest.

15. The ultrasonic diagnostic imaging system of claim 14, wherein the motion processor comprises a Doppler signal processor.

16. The ultrasonic diagnostic imaging system of claim 14, wherein the display is operated to concurrently display a two or three dimensional image containing a region of interest and a spectrogram illustrating the velocity variation over time for the region of interest.

17. The ultrasonic diagnostic imaging system of claim 14, wherein the motion processor comprises one of a phase-domain or a time-domain signal processor.

18. The ultrasonic diagnostic imaging system of claim 14, wherein the motion characteristic processor comprises a histogram processor.

* * * * *